United States Patent [19]

McMullen

[11] Patent Number: 4,816,262

[45] Date of Patent: Mar. 28, 1989

[54] CONTROLLED RELEASE TABLET

[75] Inventor: Jean N. McMullen, St. Bruno, Canada

[73] Assignee: Universite de Montreal, Montreal, Canada

[21] Appl. No.: 901,398

[22] Filed: Aug. 28, 1986

[51] Int. Cl.$^4$ ............................................. A61K 9/44
[52] U.S. Cl. ................................................... 424/467
[58] Field of Search ........................................ 424/467

[56] References Cited

U.S. PATENT DOCUMENTS

| | | | |
|---|---|---|---|
| 216,107 | 6/1879 | Richards | 424/467 |
| 2,312,381 | 3/1943 | Bickenheuser | 424/467 |
| 3,113,076 | 12/1963 | Jacobs | 424/467 |
| 3,146,169 | 8/1964 | Stephenson et al. | 424/467 |
| 3,279,995 | 10/1966 | Reid | 424/467 |
| 4,218,433 | 8/1980 | Kooichi et al. | 424/467 |
| 4,663,147 | 5/1987 | De Prince | 424/467 |

FOREIGN PATENT DOCUMENTS 1372040 12/1970 United Kingdom ................ 424/467

Primary Examiner—Shep K. Rose
Attorney, Agent, or Firm—Cushman, Darby & Cushman

[57] ABSTRACT

The disclosure herein describes a controlled release tablet which includes a core formed of a solid mixture having a hydrophilic releasable agent; the core has a central hole and is coated, on all faces except that bordering the hole with a hydrophobic material. The thickness of the core gradually increases from the hole to the outer border, this being a factor in the rate of release of the mixture through the hole. One application of such a tablet is for the controlled release of a therapeutic agent in the field of drug delivery systems.

4 Claims, 6 Drawing Sheets

CONTROLLED RELEASE TABLET

FIELD OF THE INVENTION

The present invention pertains to a tablet which includes an active agent which must be released at a controlled rate.

More particularly, the present invention pertains to a pharmaceutical tablet wherein the diffusion of a drug from a suspension must be controlled.

BACKGROUND OF THE INVENTION

It is well known that compositions of matter formed into compact bodies from which the matter can be dissociated or released for various useful purposes are known. The release of material has many applications which may be readily apparent to persons skilled in the art of material release.

One such application is found in the medicinal use of drugs administered orally or otherwise into the organic system. Diffusion-controlled matrix devices have received a great deal of attention for drug delivery systems in the past years.

One approach has been to use insoluble porous disc matrices, in which the loading of the drug is greater than its solubility limit in the dissolution medium. However, it has been found that the amount of solute which diffuses out of these flat discs is linear with the square root of time. In other words, with this system, the amount of drug available at a biological site of absorption decreases as a function of time if the absorption rate is greater than the drug release rate from the matrix.

One way to overcome this difficulty has been to vary the matrix geometry in order to ideally attain a zero-order drug release. With this thought in mind, it was suggested that a sector of a right circular cylinder could be the needed geometry. Dean S. T. Hshich and some of his colleagues in the Journal of Pharmaceutical Sciences, vol. 72, no. 1, January 1983, proposed a hemispheric structure. However, in order to adapt these systems for pharmaceutical manufacturing, considerable modifications in their fabrication procedure would have to be carried out.

Recently, it was suggested by Wei-Youh K. et al., in the Journal of Pharmaceutical Sciences, vol. 74, no. 9, September 1985, that a multiple-hole system might provide a near zero-order-release but this suggestion has not been proved efficient by any experimental data.

OBJECTS AND STATEMENT OF THE INVENTION

It is an object of the present invention to provide a new geometric form for a tablet where the rate of release of the agent is controlled in order to avoid the above-described disadvantages of present devices.

This is achieved by providing the core of the tablet, which is formed of a solid mixture of a releasable agent, with a geometry that allows a zero-order or constant release.

The present invention, therefore, relates to a tablet which comprises, in its broadest aspect, a core defining a body of a solid mixture formed of a hydrophilic releasable agent, the body displaying a central hole and having upper and lower faces and outer and inner faces, with the inner face being adjacent to the opening; the inner face is smaller than the outer face so that the thickness of the body gradually increases from the inner face to the outer face. The core is covered with a coating of hydrophobic material, the coating extending over the upper and lower faces as well as over the outer face so that release of the agent is effected only through the hole, the varying thickness of the body thus being a factor in the rate of release of the agent through the hole.

The present invention relates also to a controlled release pharmaceutical tablet which contains a therapeutic active agent which is released through the said hole.

The invention also relates to method of making such a tablet.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DESCRIPTION OF PREFERRED EMBODIMENTS

Figure 1:
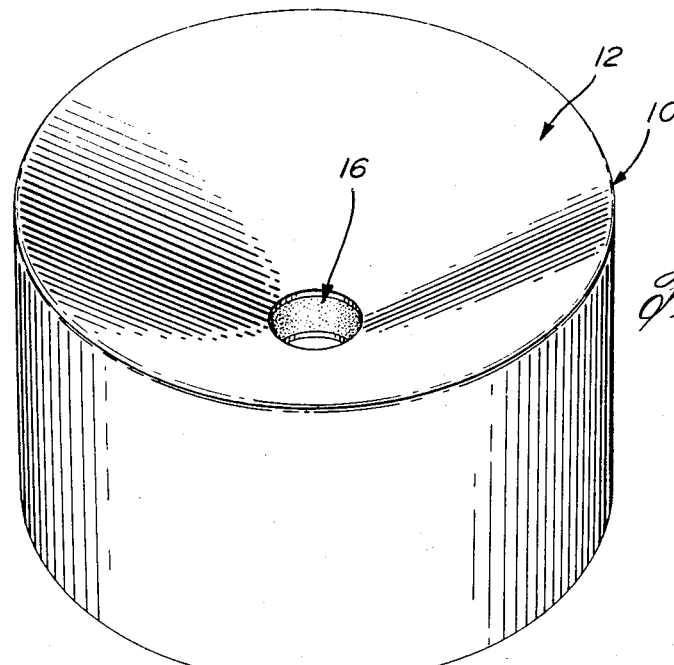
FIG. 1 shows a perspective view of a tablet made in accordance with the present invention.
Figure 2:
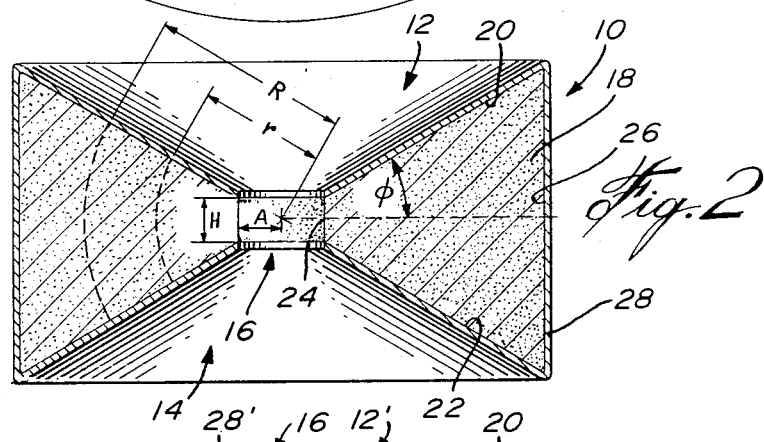
FIG. 2 is a diametrical cross-section of the tablet shown in FIG. 1.

Referring to FIGS. 1 and 2, there is shown a tablet 10 having a disc-like configuration with inwardly tapering top and bottom walls 12 and 14 and a central cylindrical hole 16.

Referring more particularly to FIG. 2, the tablet 10 includes a central core 18 formed of a solid mixture that includes a hydrophilic active agent. This core is defined by an upper annular face 20 and a lower annular face 22 and by an inner cylindrical face 24 and outer cylindrical face 26. The upper and lower faces 20 and 22 are inwardly tapering towards the center hole 16 so that the height H of the inner cylindrical face 24 is smaller than the outer cylindrical surface 26.

The upper annular face 20, the lower annular face 22 and the outer cylindrical face 26 are coated with a continuous layer 28 of a hydrophobic material so that the hydrophilic material 18, when dissolved, can only be released from the center hole 16 of the tablet.

Figure 2A:
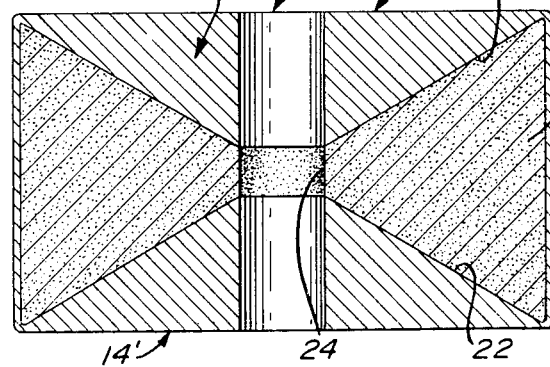
FIG. 2a is a cross-sectional view of another embodiment of a tablet made in accordance with the present invention.

FIG. 2a illustrates a variant of the tablet shown in FIG. 2 in that the coating 28' is made thicker on faces 20 and 22 so that the top annular faces 12' and 14' of the tablet are substantially parallel to one another and to the plane of the tablet.

Other geometric shapes may be given to the tablet as long as the core has a configuration corresponding to the characteristics described hereinbelow. Also, it will be evident to the persons skilled in the practice of material release to foresee the many applications of a tablet of which allows gradual release of compositions of matter, e.g. in the distribution of chemicals for agricultural purposes or other purposes where chemical substances are needed in a continuous but gradual application.

However, the present disclosure will hereinbelow be continued in relation to the field of drug release in which it is desired to control the release of a therapeutic active agent for administration orally or otherwise into an organic system.

Referring to FIG. 2, the distance of the dissolution front 24 to the center of the hole is given by R; $\phi$ is the angle between the face 20 and a horizontal plane passing through the mid-height of the disc; r is the region bounded by $A<r<R$. All these parameters are critical in the obtention of a constant release.

For the inwardly tapered disc of the present invention, there is two geometric parameters that can be easily controlled, A and $\phi$.

Figure 3:
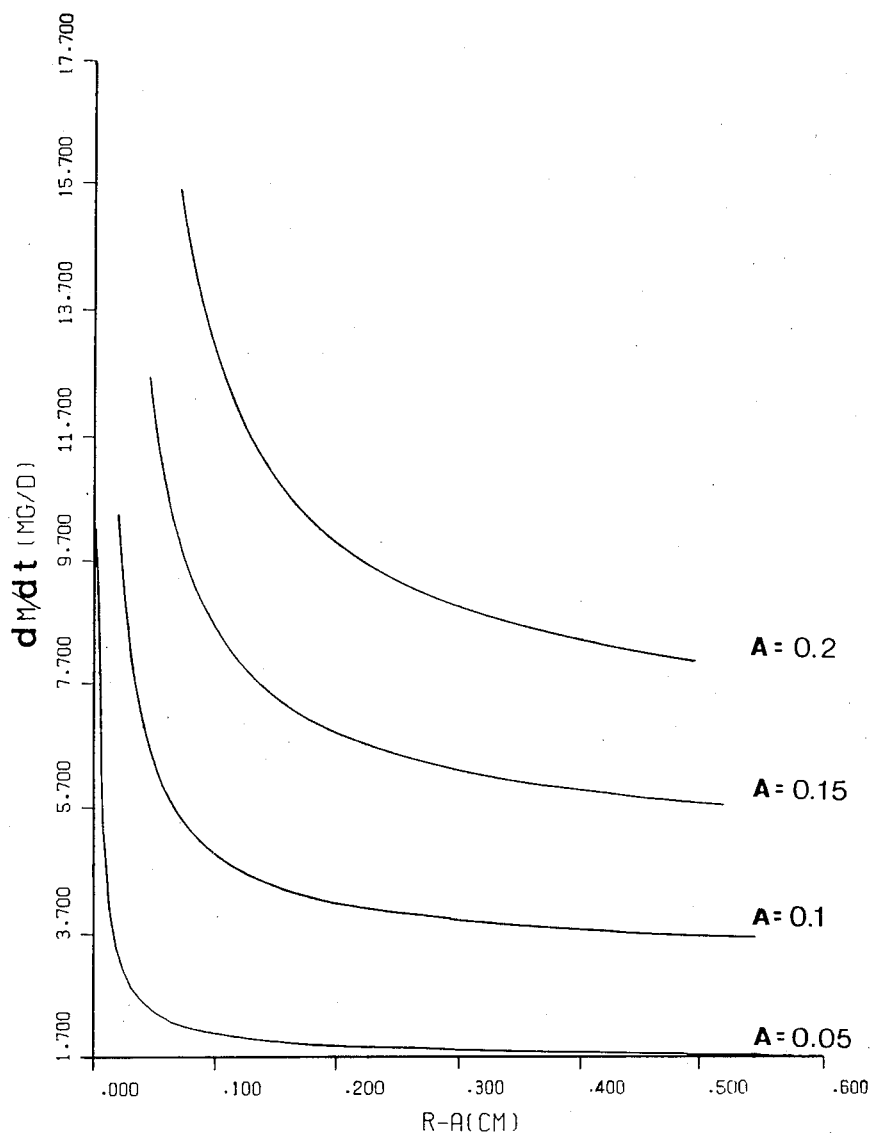
FIG. 3 is a graph showing the release rate as a function of the dissolution front.

FIG. 3 shows the effect of A, at constant $\phi$ equal to 30°. In all cases, the release rate is initially high and rapidly drops as the dissolution front recedes. At $R>2A$, nearly constant values are obtained, with smaller holes giving a better zero-order approximation. It can be seen that when A increases from 0.1 to 0.2, giving a fourfold surface area increment, the release rate does not increases by the same factor. This indicates that the mass flux (J) decreases as A is increased. This point is further illustrated in FIG. 4, and is the result of a faster displacement of the dissolution front as A is increased.

Figure 4:
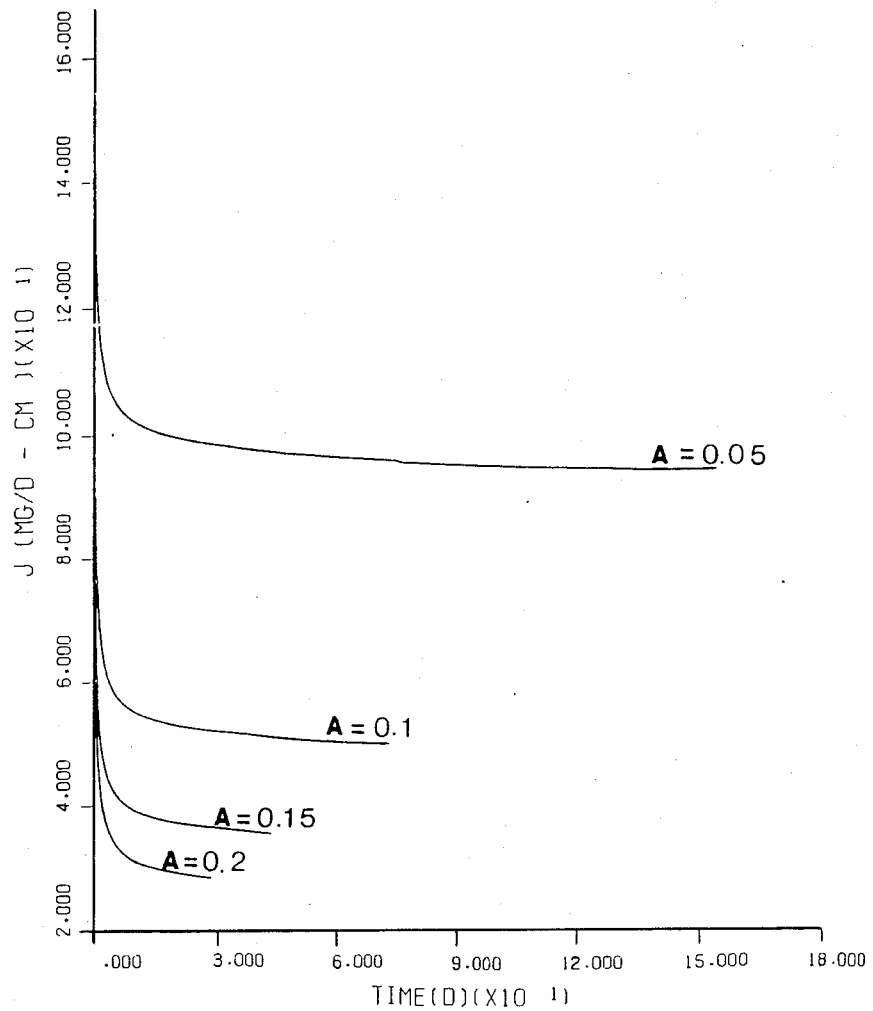
FIG. 4 is a graph showing profiles of the mass flux as a function of time.

FIG. 4 shows J profiles as a function of time for different values of A. Curves of constant A, for discs having various angles, are superimposable, which indicates that J is not influenced by $\phi$. However, $dM_r/dt$ will increase with $\phi$, because higher $\phi$ values are associated with higher surface areas.

The following equations:

$$M_r = 4\pi \sin[\phi]\epsilon \left[ \frac{\rho[R^3 - A^3]}{3} - C_s R \left[ \frac{[R^2 - RA + A^2]}{3} - \frac{A[R + A]}{2} \right] \right]$$

$$t = \frac{\sin[\phi]}{HD'} \left[ \frac{2\rho[R^3 - A^3][R - A]}{3C_s R} - \left[ \frac{2[R^3 - A^3]}{3} - A[R^2 - A^2] \right] \right]$$

where:
A, R, $\phi$ and H have been previously defined;
$C_s$ is the solute solubility in the dissolution fluid at a given temperature;
D' is the solute diffusion coefficient in the dissolution fluid, divided by the tortuosity (T) of the matrix pores;
$\epsilon$ is the final volumetric porosity;
$M_r$ is the mass of solute released;
t is the time;
$\rho$ is the solid solute density;

can be used for the design of a particular system in order to meet a desired kinetic. Each of the parameters can be easily determined, including D', which can be computed from sorption-desorption experiments carried out with standard flat discs. These sorption-desorption experiments can be done following the technique described by Desai et al in J. Pharm. Sci., 1966, 55, 1224-1229.

The properties of the different components used to prepare a tablet are important in order to ensure constant release.

In the case of a pharmaceutical tablet, the coating has to be hydrophobic and inert to gastro-intestinal juices. Any polymer accepted for human consumption that meet these requirements, such as polyethylene, caprolactone and EVAC among others, can be used. In the case of an implant, however, the as well as the coating used has to be compatible and/or bio-degradable as are, for example, EVAC and caprolactone.

There are two other critical features for the obtention of a constant release.

First, the angle of the two inwardly tapered surfaces is a critical criteria as it will be shown in further examples.

There is also an important relationship between the polymer matrix and the volume of drug that is incorporated within, which means that when the drug concentration is low, an inert soluble filler has to be added in order to arrive at a certain minimum volume, below which constant release is differert to achieve. On the other hand, the volume of drug used can go up to 100%, although, in that case, dissolution is much faster but can still be controlled by varying the hole diameter.

The following examples illustrate the present invention without, however, limiting the same thereto. Sodium salicylate and polyethylene powder were used as models for the therapeutic agent and polymer matrix, respectively. Sodium chloride, potassium phosphate monobasic and sodium phosphate dibasic were of reagent grade and used as is for buffer preparation. Sodium azide was used at a 0.02% concentration in the buffer, to inhibit microbial growth.

EXAMPLE 1

A 60% w/w sodium salicylate-polyethylene mixture was blended in a Turbula (type T2C, Bachofen A. G. -Switzerland) mixer for 20 min. and sieved (50 mesh, U.S.P.) twice to obtain an homogeneous mixture. An aliquot of this blend (0.5-0.7 g) was then transferred into a tempered steel die, 1.27 cm in diameter, preheated at 150° C. for 30 min., and heated for a further 15 min. in order to melt the polyethylene. The die containing the mixture was then transferred to a Carver laboratory press and compressed at 175 MPa for 2 min. with the use of a stainless steel flat and circular conic punches having an angle of 20° with an axis perpendicular to the cone. After compression, a 30 min. cooling period at room temperature, was allowed to permit polyethylene to solidify. Matrices were then removed from the die, weighed and their peripheric thickness measured with a micrometer. For the coating procedure, a nickel-chromium thread, 0.4 mm diameter, was introduced 2 mm in depth in the peripheric surface of each matrix. Matrices were then dip-coated with approximately 6–8 coats of paraffin wax (80° C.), in order to cover all edges. Central holes were made by a 0.150 cm radius stainless steel drill bit mounted on a precision drill press (model 7000, Servo Prod. Co., CA) set at 500 rpm. Matrices were centered under the drill bit, held firmly, and perforated in less than 5 sec in order to prevent excessive heat build up. Matrices were then stored in total darkness. Each matrix initially contained 287 mg of sodium salicylate.

EXAMPLE 2

The matrices of Example 2 were prepared by following the procedure of Example 1, the only difference being the use of a conic punch having an angle of 30°. Each matrix initially contained 400 mg of sodium salicylate.

Figure 5:
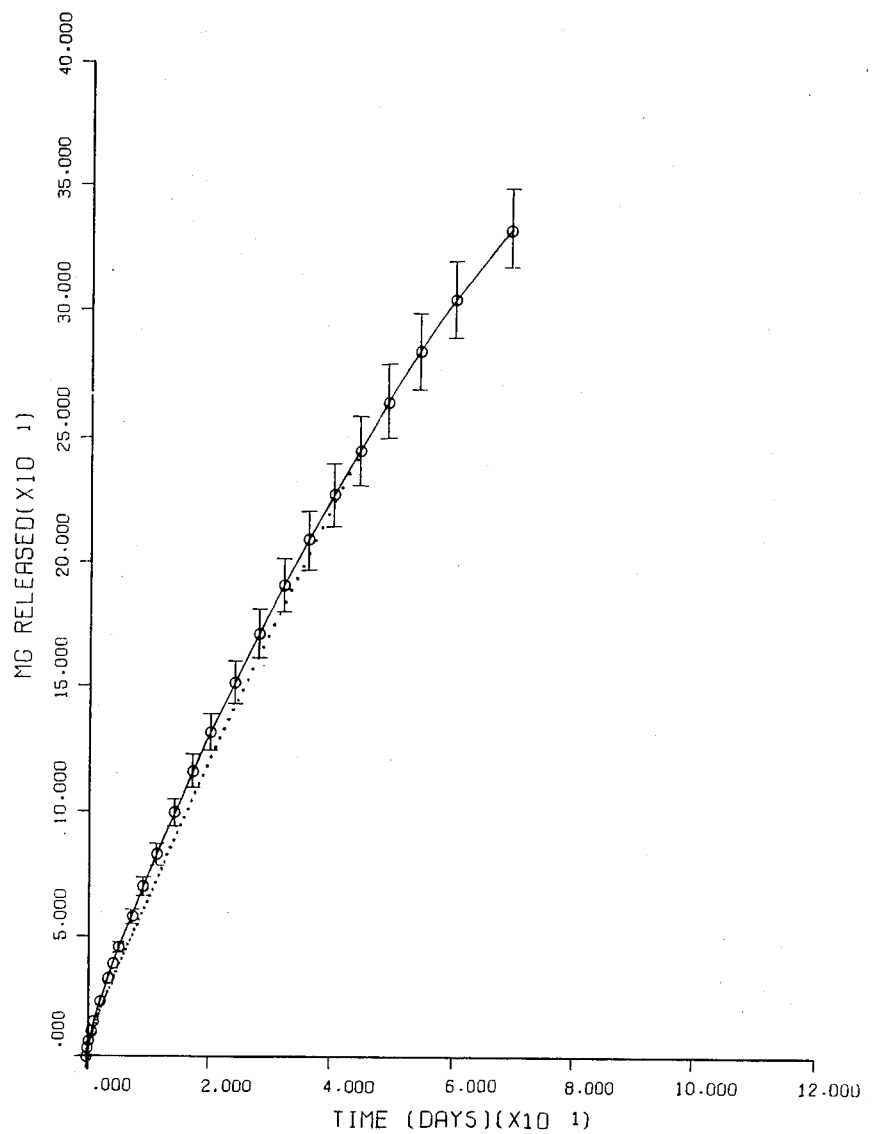
FIG. 5 is a graph showing sodium salicylate cumulative amounts released as a function of time for discs having 30° angle.
Figure 6:
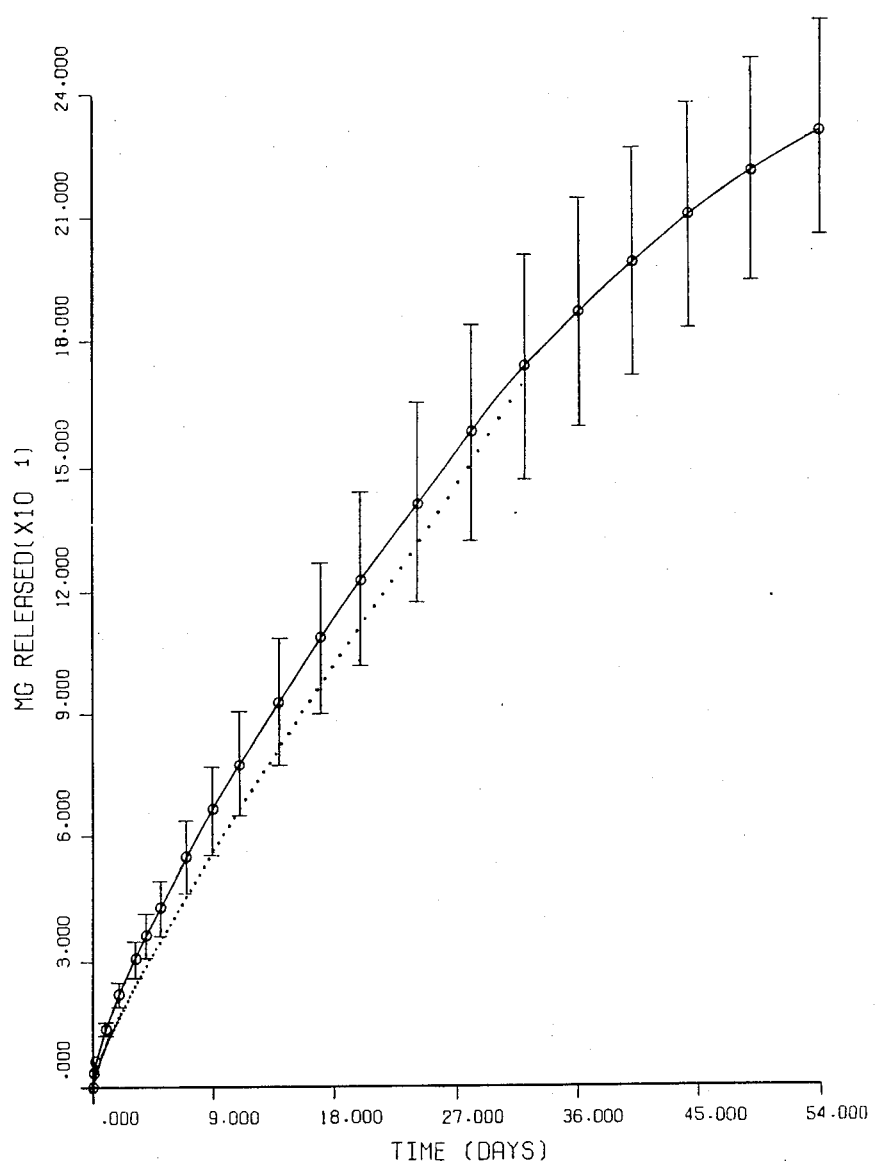
FIG. 6 is a graph showing sodium salicylate cumulative amounts released as a function of time for discs having 20° angle.
Figure 7:
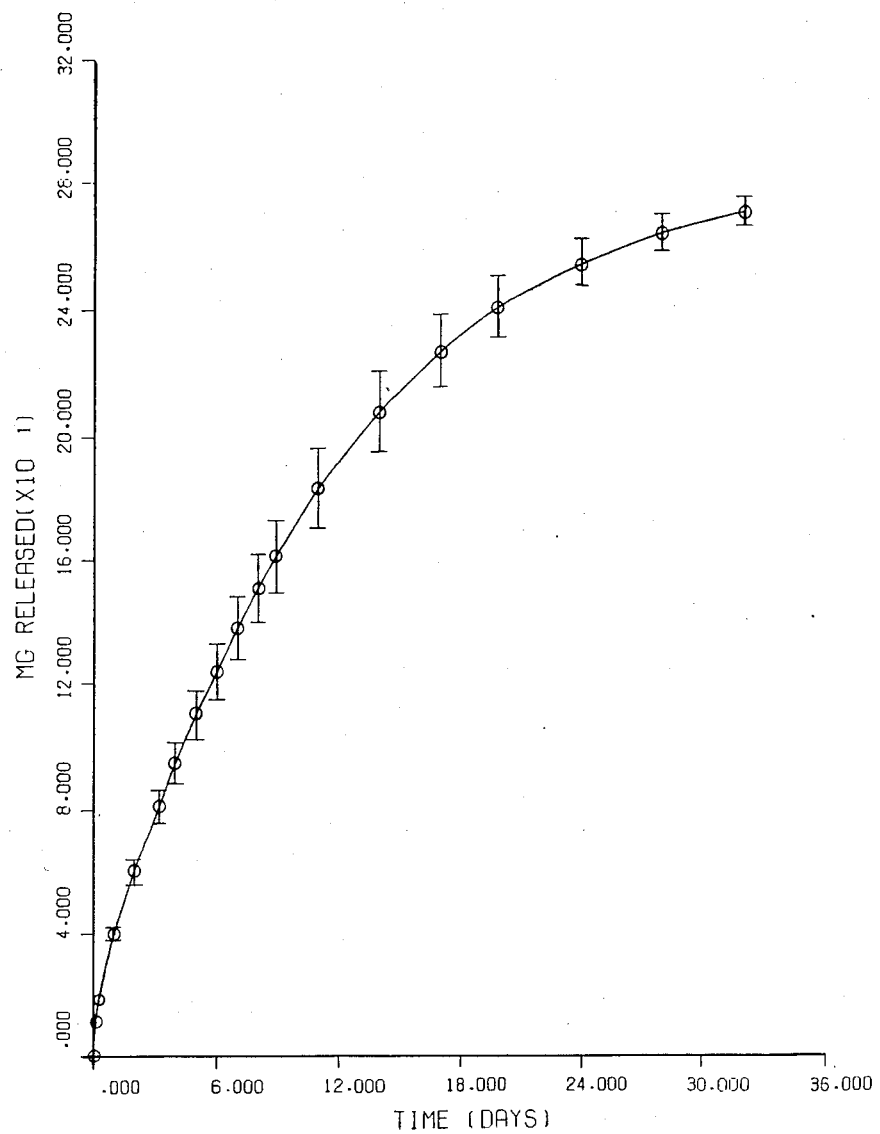
FIG. 7 is a graph showing sodium salicylate cumulative amounts released from a flat disc with a central releasing hole.

FIGS. 5 and 6 show plots of experimental and model predicted cumulative amounts of sodium salicylate released as a function of time, for the 30° and 20° discs, respectively. There is a good agreement between experimental and model predicted data. FIG. 7 shows experimental data for flat discs. Unperforated matrices released less than 0.6 mg in 25 d, demonstrating that the solute release only occurs through the central cylindrical surface. The tapered discs show an evident deviation from a stricly zero-order release. However, after the initial high release rate, which represents less than a 0.1 fraction of mass released (F), linearity is almost achieved.

Although the invention has been described above in relation to two specific examples, it is believed that it may be refined and modified in various ways. It is therefore wished that the present invention showed not be limited in interpretation except by the terms of the following claims.

The embodiments of the invention in which an exclusive property or privilege is claimed are defined as follows:

1. A pharmaceutical tablet comprising:
    a body having a disc-like configuration with a cylindrical hole extending centrally therethrough, said body including:
    a core formed of a compressed mixture of a therapeutic agent and of a biocompatible polymeric material, said core being defined by centrally tapering upper and lower annular faces and by inner and outer cylindrical faces; and
    a coating of impermeable material covering said upper and lower annular faces and said outer cylindrical face; said agent being released from said hole at a biological site of absorption.

2. A pharmaceutical tablet as defined in claim 1, wherein said coating on said upper and lower annular faces defines flat upper and lower surfaces extending in a plane subtantially parallel to that of said body.

3. A pharmaceutical tablet as defined in claim 1 or 2, wherein said annular faces define an angle of 30° relative to the plane of said body.

4. A pharmaceutical tablet as defined in claim 1 or 2, wherein said annular faces define an angle of 20° relative to the plane of said body.

* * * * *